United States Patent [19]

Hoskinson et al.

[11] Patent Number: 5,109,026
[45] Date of Patent: Apr. 28, 1992

[54] 2-COMPONENT IMMUNOADJUVANT

[75] Inventors: Ronald M. Hoskinson, Normanhurst; Robin D. G. Rigby, Winmalee; Phillip E. Mattner, Epping, all of Australia

[73] Assignee: Commonwealth Scientific and Industrial Research Organization, Campbell, Australia

[21] Appl. No.: 335,088

[22] Filed: Apr. 17, 1989

Related U.S. Application Data

[63] Continuation of PCT/AU87/00250, Aug. 15, 1987.

[30] Foreign Application Priority Data

Aug. 15, 1986 [AU] Australia ............... PH7459

[51] Int. Cl.$^5$ .............................. A61K 47/00
[52] U.S. Cl. ...................... 514/777; 514/788; 514/939
[58] Field of Search ............... 424/88; 514/777, 939, 514/788

[56] References Cited

U.S. PATENT DOCUMENTS 4,258,029  3/1981  Moloney et al. .............. 424/88

FOREIGN PATENT DOCUMENTS 0059521  8/1982  European Pat. Off. .
1089767  11/1967  United Kingdom .
2166951  5/1986  United Kingdom .

OTHER PUBLICATIONS

Derwent Abstract Accession No. 85-097598/16, Class D16, SU, A, 1115-754 (MOSC MED PIROGOV), Sep. 30, 1984.

Bach, Jean-Francois (Ed) 'Immunology', published 1978, by John Wiley & Sons Inc. (USA), see pp. 815-816.

Woodward L. F. & Jasman R. L., 'Stable Oil-in-Water Emulsions: Preparation and use as Vaccine Vehicles for Lipophilic Adjuvants' Vaccine, vol. 3, Jun. 1985, pp. 137-144.

*Primary Examiner*—Frederick E. Waddell
*Assistant Examiner*—Diane Gardner
*Attorney, Agent, or Firm*—Fleit, Jacobson, Cohn, Price, Holman & Stern

[57] ABSTRACT

An immunoadjuvant capable of producing secondary antibody responses as great as 50 to 60% of those obtained using Freund's complete adjuvant (FCA) which responses decline at a slow rate while not showing the disadvantages associated with FCA. The immunoadjuvant comprises an immunoadjuvant oil such as a mineral oil, squalene or squalane and a polycationic polyelectrolyte immunoadjuvant such as DEAE-Dextran or polyethyleneimine. The immunoadjuvant preferably comprises an emulsion having the oil in one phase and an aqueous solution of the polycationic polyelectrolyte in the other phases. Such immunoadjuvants are used with antigens, such as conjugates of hormones, e.g. luteinizing hormone releasing hormone, and an immunogenic protein.

5 Claims, 5 Drawing Sheets

2-COMPONENT IMMUNOADJUVANT

CROSS REFERENCE TO RELATED APPLICATION(S)

This U.S. application is a continuation of PCT International application No. PCT/AU87/00250 filed Aug. 15, 1987.

TECHNICAL FIELD

This invention is concerned with immunoadjuvant compositions and their use in vaccines to stimulate animal immune systems to produce antibodies.

BACKGROUND ART

It is known that a variety of molecular species stimulate the production of antibodies in animals and are thus considered to be immunogenic or antigenic. These molecular species are mostly proteins. It is further known that antibodies may be produced in animals against non-antigenic molecules by the conjugation of those molecules with a known immunogen and vaccinating the animals with the immunogenic conjugate so formed. This immunogenicity of a molecular species may be enhanced by the simultaneous administration of an immunoadjuvant i.e. a material which while not being immunogenic itself potentiates or enhances the animals immune response to the challenging immunogen.

In the art of animal vaccination a subject of continuing interest is the identification of substances that are immuno-adjuvants, and while many such substances, both organic and inorganic, are known, the operative mechanisms involved frequently are only poorly understood.

The continuing wide interest in the discovery of effective immunoadjuvants lies partly in the traditional objective of improving the immunological properties of vaccines that provide protective immunity of animals against pathogenic organisms. A newly emerging objective lies in the perception that novel endocrine-directed vaccines have the potential to directly enhance the productivity of livestock by mechanisms that are entirely unrelated to health maintenance In this field researchers aim to manipulate animal physiology by conferring selected and controlled hormone-specific autoimmunity so that hormonal mechanisms that inhibit productivity can be suppressed. This new field, that could be described as that of "hormonal autoimmunity", differs from classical vaccinations to achieve protective immunity, in that the immunological objective is to achieve effective autoimmunity against specific hormones expressing a limited range of epitopes or even a single epitope. The antigens of this newer field are thus hormones or structural elements of hormones.

Compared to the vast amount of prior art in the field of vaccines for protective immunity the prior art in the field of "hormone-specific autoimmunity" is relatively small. While the present invention is not limited to the field of hormone autoimmunity it nevertheless is of particular relevance to that field of vaccine research.

A common reference immunoadjuvant standard in this field is Freund's Complete Adjuvant (FCA), which comprises a suspension of heat killed *M.tuberculosis* mycobacteria in mineral oil containing surfactant. Although generally recognised as one of the most powerful immunoadjuvants presently available, FCA has not found wide application outside the laboratory because of the adverse tissue reaction it provokes in recipient animals. FCA is inclined to induce the production of granulomateous lesions in animals at the site of the immunisation. It has also been found that cattle that have been injected with FCA test positive for tuberculosis, when, in fact they may never have been invaded by live and hence infectious *M.tuberculosis* organisms. It is thus of considerable commercial importance to discover safe effective alternatives.

Two immunoadjuvants known in the art are: (1) mineral oils and vegetable oils, used in conjunction with emulsifiers but without added mycobacteria and (2) the water-soluble polycationic polyelectrolytes such as diethylaminoethyl dextran (DEAE-dextran). The immunoadjuvant oils have immunostimulatory characteristics that are distinct and recognizably different from those of the water soluble polycationic immunoadjuvants. For example, when animals are treated with vaccines formulated into emulsions with oily mycobacteria-free immunoadjuvants, there is a pattern of weak secondary antibody response peaking commonly at 10-20% of that attainable with FCA, but which may nevertheless persist for several months. On the other hand the water-soluble polycationic polyelectrolytes can, under the most favourable circumstances, provoke strong secondary antibody responses, of the order of that when FCA is used, but the responses decline rapidly from peak values.

Those familiar with the art will recognise that these foregoing comparisons with FCA are descriptive of the general kinds of effects that are obtained with mineral oil emulsion adjuvants on one hand and water soluble polyelectrolyte adjuvants on the other. They are clearly not intended to quantify all possible comparisons of this kind in relation to FCA because, in practice, many factors other than the nature of the component immunoadjuvant in a vaccine influence the pattern of the antibody response to vaccination.

Nevertheless while the two important classes of immunoadjuvants that have been described above can usefully enhance immune antibody responses, the value of each class has been limited by the aforesaid characteristics, and the art has lacked an immunoadjuvant which can initially provoke a strong response and yet sustain something more than a modest response for an extended period.

DISCLOSURE OF THE INVENTION

It is an object of this invention to provide immunoadjuvant compositions which when used to formulate vaccines which fill the gap in the prior art between those inducing high peak/short life antibody responses and those inducing low peak/long life responses.

The present invention consists in an immunoadjuvant comprising an immunoadjuvant oil substantially free of mycobacteria and a polycationic polyelectrolyte immunoadjuvant.

In preferred embodiments the invention consists in an immunoadjuvant being an emulsion having in one phase the oil substantially free of mycobacteria and in the other phase an aqueous solution of the polycationic polyelectrolyte. In another aspect the present invention consists in a method for the vaccination of an animal against an antigen the improvement comprising administering the antigen to the animal in association with an immunoadjuvant oil substantially free of mycobacteria and in association with a polycationic polyelectrolyte immunoadjuvant.

The secondary antibody responses obtained following a sequence of two vaccinations using the immunoadjuvant according to this invention can reach peak values as great as 50-60% of those using FCA, such peak values decline at a slow rate that is more characteristic of responses attained using oil adjuvants than when using polyelectrolyte solutions. It is a feature of this invention that its hitherto unattainable antibody response profile is not merely the sum of the profiles that would be obtained by use of the components separately, rather, there is a mutual augmentation of the separate immunoadjuvant activities when the components are jointly presented to recipient animals in the novel compositions and novel vaccines of the invention. In consequence the antibody response profile exceeds the sum of the response profiles that is obtained by use of each of the component immunoadjuvants separately.

It will be understood by those skilled in the art that emulsified compositions according to preferred embodiments of this invention are compositions which are stable and resistant to segregation into their component oil and aqueous phases. It is preferred that the emulsions are of the water-in-oil type though the oil-in-water type could be used. While the invention can be extended to embrace a wide range of oils with which to form its novel compositions, including both mineral and vegetable oils, the preferred oils are those mineral oils already known in the art and including substances such as Drakeol, Markol, squalene, squalane and the like. It is well known that immunoadjuvant emulsions of individual oils used separately can be designed and formulated with oil to water phase ratios extending over a broad range and embracing the ratios 80:20 to 20:80 (v/v) for example. Such a broad range of ratios of oil phase to aqueous phase also applies in the present invention except that the aqueous phase will always be comprised of a polycationic polyelectrolyte solution, typically 5-25% (w/v) and preferably of near neutral pH. The emulsifiers used to form the novel compositions of the invention are those known to the art and typified by the well known Arlacel products and including Arlacel A and Arlacel 80 as oil-soluble emulsifiers and Tween 80 as a water-soluble emulsifier.

While the preferred immunoadjuvants according to this invention are emulsions it is to be noted that mixtures, suspensions, solution and co-solutions could all be used instead of emulsions. In fact the advantages of the invention may be obtained by administering to an animal separately but in association an antigen, the oil and the polyelectrolyte. In this respect the expression "in association with" is taken to mean that the various components are physiologically active in the animal at the same time whether administered simultaneously or sequentially.

The polycationic polyelectrolytes of the invention are those whose aqueous solutions are known to have or that can be shown to have immunoadjuvant properties. Diethylaminethyldextran (DEAE-dextran) is a preferred example because of its current suitability for veterinary vaccines. It is a part of the novelty of this invention that the simple polycation, polyethyleneimine is an effective immunoadjuvant and when used according to the compositions of this invention is capable of potentiating useful anti-hormone antibody responses in vaccinated animals.

Because of their efficacy and the minimal tissue reactions they provoke the immunoadjuvant compositions of the invention have particular application to the management of anti-hormone immunity in livestock.

Accordingly it will be recognised that the invention embraces vaccines comprised of its novel immunoadjuvant compositions together with an antigen and, in particular, antigens designed to confer anti-hormone immunity.

Such antigens will be frequently, but not always, hormone:protein conjugates where the hormone may be any known in the field of endocrinology and including gonadal steroids, glucocorticoids, hypothalamic releasing factors such as luteinizing hormone releasing hormone (LHRH), neuroendocrine peptides such as the enkephalins and somatostatin and gut peptides such as gastrin. The immunogens used in the novel compositions of the invention could also be growth factors or their conjugates or they could be conjugates of fragments of protein or peptidic hormones chemically linked to immunogenic carrier proteins.

BRIEF DESCRIPTION OF THE DRAWINGS

Hereinafter given by way of example only are preferred embodiments of the present invention described with reference to the accompanying drawings in which.

BEST MODE OF CARRYING OUT THE INVENTION

Figure 1:
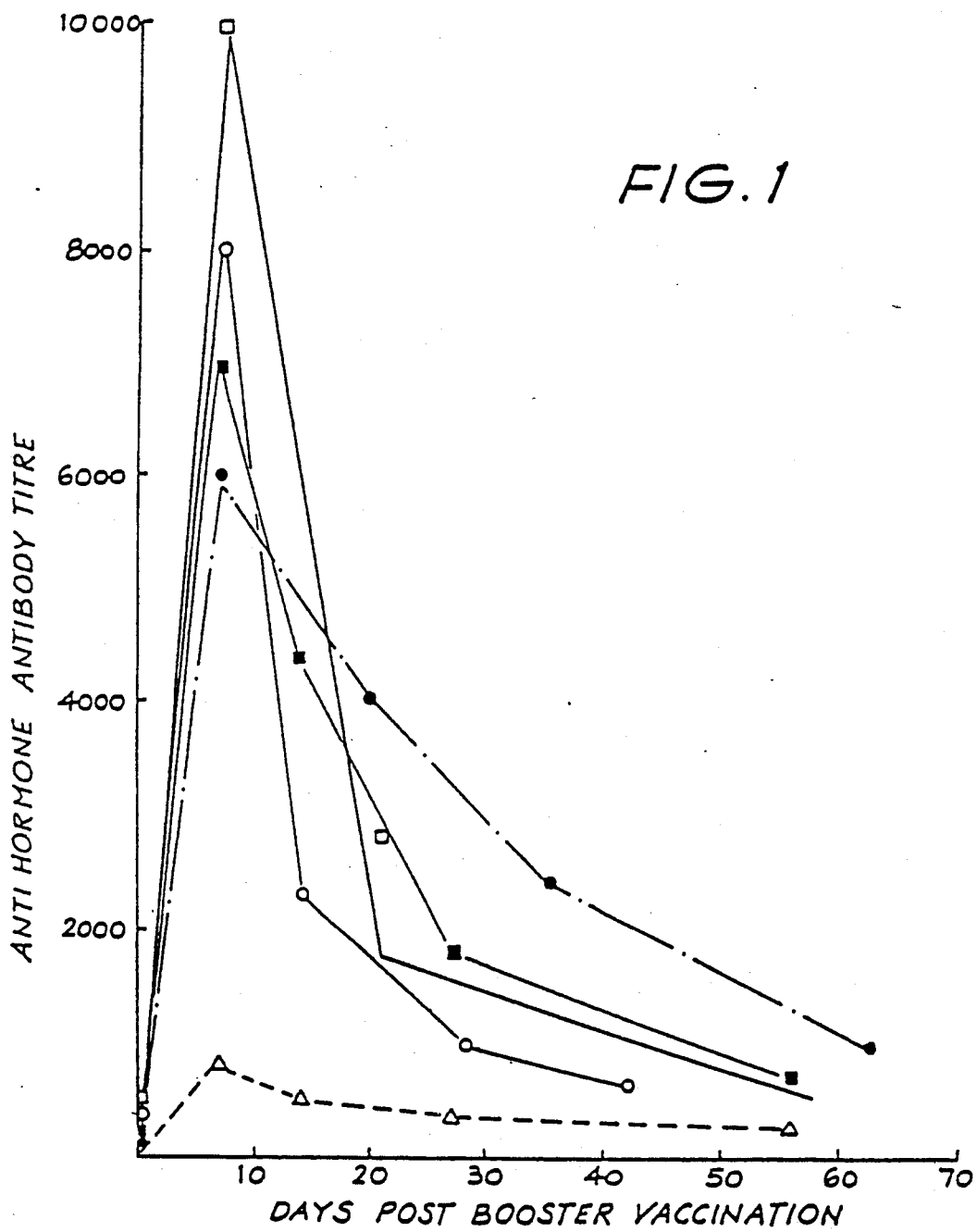
FIG. 1 shows the relationship between anti-hormone antibody titres and time, characteristics of known vaccines.

In all the following examples the antigens with which the relevant vaccines were formulated were hormone:protein conjugates. They were synthesized by conjugation of hormonal acid derivatives to serum albumins with diimide reagents by procedures known in the art. Antisteroid or anti-LHRH antibody titres recorded on the Figures are mean reciprocal antibody titres measured according to the procedure of G. E. Abraham (Acta. Endocr., 1974, 75, suppl. 183,7) using [$^3$H]-steroids or $^{125}$I-LHRH (specific activity 3.7 TBq/m mole) as radio ligand. In this procedure immune plasma was diluted serially with sodium/potassium phosphate buffer (0.05M, pH 7.4) containing gelatin (0.1%), sodium chloride (0.9%) and sodium azide (0.1%). Radiolabelled hormone (185 Bq, 10 pg) in 50 μl phosphate buffer was added to each dilution to make a final volume of 1.0 ml. The mixture was kept at 4° C. (16 h) and dextran-coated charcoal added (0.1 ml consisting of 2% (w/v) decolourizing charcoal) suspended in phosphate buffer containing 0.1% (w.v) dextran T-70. After centrifugation to pellet the charcoal, the radioactivity in the supernatant liquid was measured by beta or gamma counting. The antibody titre is defined as the dilution of antiserum which bound 50% of the radiolabelled hormone available and is expressed as the reciprocal.

EXAMPLE 1

Prior Art Antihormonal Antibody Response Profiles Induced By Vaccination With Deae-Dextran Or By Mineral Oil Emulsion Adjuvants This example is to illustrate, for reference, gross features of the prior art.

Five vaccines were prepared and their composition on a single dose basis (2 ml) is given in the following. Vaccines 1–4 were all aqueous solutions containing DEAE-dextran adjuvant. Vaccines 1–3 consisted of steroid human serum albumin conjugate (1 mg) dissolved in 5% DEAE-dextran solution (pH 7, 2 ml). The steroid derivatives used to form the antigen conjugates were androstenedione-7-α-carboxyethylthioether, testosterone-3-CMO and oestradiol-17β-6-CMO respectively.

Vaccine 4 consisted of an LHRH free acid LHRH[1-9]glyOH):human serum albumin conjugate (1 mg) dissolved in 5% DEAE-dextran solution (pH 7, 2 ml).

Vaccine 5 (Mineral oil adjuvant emulsion) was prepared by dissolving androstenedione-7-α-carboxyethylthioether: human serum albumin conjugate (1 mg) in saline (0.37 ml) and Tween 80 (0.02 ml). This aqueous phase was subsequently emulsified by vortexing with mineral oil (1.45 ml) containing Arlacel 80 (0.16 ml).

Five groups of sheep, each comprising 5 Merino ewes were vaccinated with Vaccines 1–5 respectively. Each vaccination consisted of 2 ml vaccine given subcutaneously in the neck region at a single site.

A primary was followed by single booster vaccination 28 days subsequently. Plasma samples were obtained from each ewe at the day of boost and then approximately 7, 14, 28 and 56 days thereafter. The antihormone antibody titre was measured in each plasma sample and the means for each vaccine shown on FIG. 1.

Vaccines 1–4 illustrate the classic antihormone antibody response profile due to the water-soluble DEAE-dextran adjuvant. Coincidentally the anti-steroid antibody responses are so similar they can almost be fitted to a single curve.

This example is given to draw attention to certain aspects of the prior art in the field of hormone specific autoimmunity. The example illustrates the fact that across a surprising range of hormone:protein conjugates the pattern of the anti-hormone antibody response is remarkably similar following similar sequences of primary and booster vaccinations with vaccines adjuvanted with the polycationic polyelectrolyte DEAE-dextran. The principal feature is the small primary response, rapid boost response which quickly peaks and quickly declines so that at about 50 days post boost the prevailing antibody titres are only about 10% of peak values. Furthermore, the example through vaccine 5 illustrates a common feature of simple mineral oil emulsion vaccines in the potentiation of a low but persistent antihormone antibody response.

EXAMPLE 2

Demonstration Of Mutual Adjuvant Augmentation (Synergism) And Specific Antihormonal Antibody Enhancement By A Novel Composition Of The Invention Three vaccines, each containing as antigen a conjugate of LHRH free acid LHRH [(1-9) glyOH] with human serum albumin, were prepared with the following compositions per 2 ml dose:

Vaccine 1 (DEAE-dextran solution immunoadjuvant) contained antigen (1 mg) dissolved in 2 ml of 7.5% DEAE-dextran solution pH 7.5.

Vaccine 2 (DEAE-dextran emulsion immunoadjuvant) contained antigen (1 mg) dissolved in 1 ml of 15% DEAE-dextran solution emulsified with squalene (0.7 ml) containing dissolved Arlacel 80 (0.3 ml). The emulsion was prepared by slow addition of the aqueous phase to the vortexed oil phase to produce a stable emulsion phase.

Vaccine 3 (Squalene emulsion immunoadjuvant) contained antigen (1 mg) dissolved in saline (1 ml) and emulsified with squalene (0.7 ml) containing dissolved Arlacel 80 (0.3 ml) in the same manner as Vaccine 2.

Figure 2:
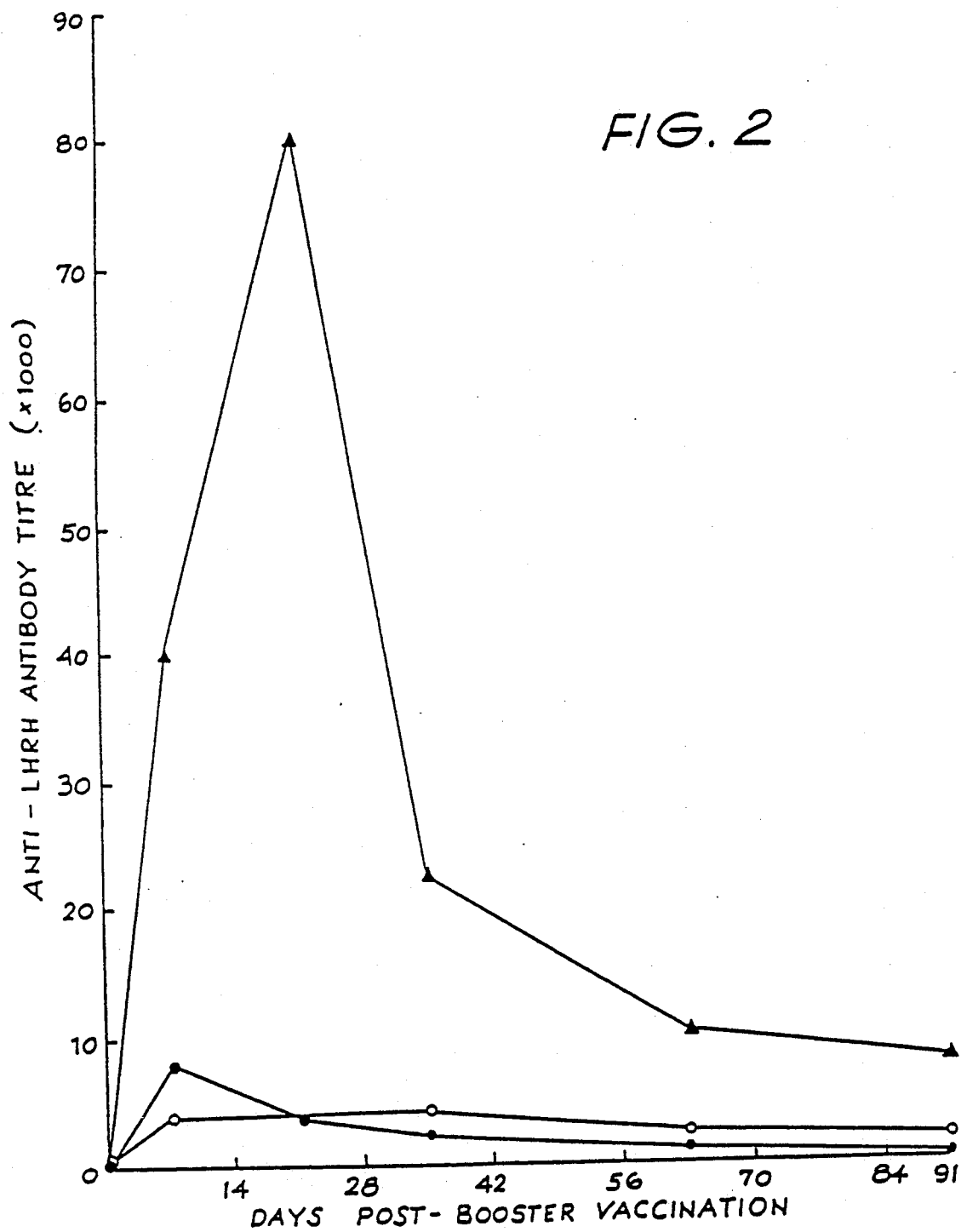
FIG. 2 shows the relationship of anti-LHRH antibody titres and time for these vaccines including one vaccine according to the present invention.

Three groups of sheep each comprising 8 Merino ewes were vaccinated with Vaccines 1, 2 and 3 respectively. Each vaccination consisted of 2 ml vaccine given at a single intramuscular site in the hind leg. A primary vaccination was followed by a booster 13 weeks subsequently. A blood sample was withdrawn by jugular venepuncture from each ewe on the day of boost and then 7, 21, 35, 63 and 91 days post boost. The anti-LHRH antibody titre in each blood plasma sample was measured and mean values for each vaccine shown on FIG. 2.

Vaccines 1 and 3 are representative of the prior art and illustrate relatively faster and slower rates of decline of anti-LHRH antibody titre respectively, subsequent to the peak boost response. Vaccine 2 is representative of the new art of this invention.

This example illustrates the essence of the invention, that is, the surprising observation that by combining two classes of immunoadjuvant already known in the art into an emulsion and the use of that emulsion in a vaccine to immunise animals, there results a mutual augmentation of the individual immunopotentiating capabilities of the components and the expression in the vaccinated animal of an enhanced and prolonged antibody response. It is thus a feature of the invention that its novel immunoadjuvants potentiate antibody responses in vaccinated animals that exceeds the sum of the responses that can be ascribed to the individual components separately.

EXAMPLE 3

Comparison Of A Novel Vaccine With Prior Art FCA And Mineral Oil Emulsion Vaccines Three vaccines, each containing as antigen an oestradiol i.e. 17β-6-CMO:human serum albumin conjugate were prepared with the following compositions per 3 ml dose:

Vaccine 1 (Freund's complete adjuvant) was prepared by dissolving antigen (1 mg) in saline and adding to vortexed FCA to form a first emulsion. To the first emulsion so formed was added 1% Tween 80 solution (1 ml) with further vortexing to provide a prior art double emulsion of FCA.

Vaccine 2 (DEAE-dextran emulsion immunoadjuvant) was prepared by dissolving antigen (1 mg) in 15% DEAE-dextran solution pH 7.5 (1 ml). The resulting solution was added to and vortexed with a solution of mineral oil (0.81 ml) containing Arlacel 80 (0.19 ml). To this first emulsion so formed was added 1% Tween 80 solution (1 ml) with further vortexing to provide a novel vaccine composition of the invention.

Vaccine 3 (Mineral oil emulsion immunoadjuvant) was prepared in the same manner as Vaccine 2 with the exception that the 15% DEAE-dextran solution was substituted with saline. The final vaccine can be regarded as a prior art double emulsion mineral oil vaccine.

Figure 3:
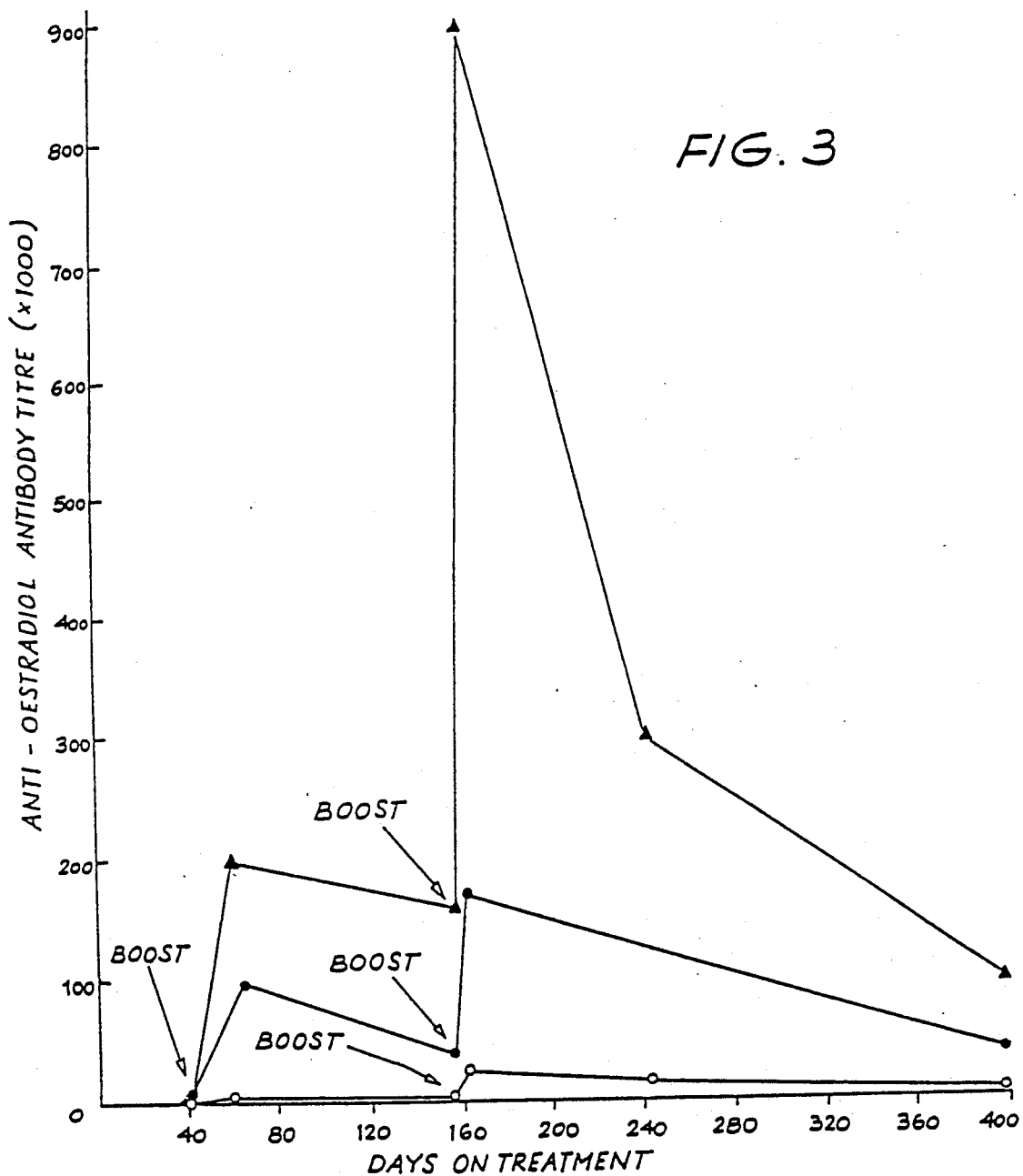
FIG. 3 shows the relationship between anti-oestradiol antibody titres and time following two booster vaccinations for three vaccines including one vaccine according to the present invention.

Three groups of sheep each comprising 25 crossbred ewes were vaccinated with Vaccines 1, 2 and 3 respectively. Each vaccination consisted of 3 ml vaccine given as 1×1 ml, intramuscularly, to each hind leg and a further 1 ml distributed subcutaneously over 6 lumbar sites. A primary vaccination was followed by boosters at 40 and 152 days subsequently. Plasma samples were obtained from each ewe at days 40, 60, 152, 164, 244 and day 400 of treatment. The anti-oestradiol antibody titre was measured in each plasma sample and the mean for each vaccine shown on FIG. 3.

Vaccines 1 and 3 are representative of the prior art and illustrate the prior art anti-oestradiol antibody responses obtainable with simple emulsified mineral oil adjuvanted vaccines (Vaccine 3) and when such vaccines are supplemented with mycobacteria to form the classical FCA emulsion vaccine (Vaccine 1). Vaccine 2 is representative of the new art of this invention.

This example illustrates the advantages of the new art of the invention in another way. Here the efficacy of a DEAE-dextran—mineral oil emulsion vaccine is compared with a separately emulsified mineral oil vaccine and with FCA. Freund's complete adjuvant is thus a benchmark for what is desirable in terms of the biological activity of an adjuvant. The prior art emulsion vaccine using mineral oil alone is a composition that may often be regarded as ineffective. It is clear that the composite vaccine of the new art, while not reaching the efficacy of FCA is substantially more effective than prior art mineral oil vaccines and accordingly within the range of commercially useful immunoadjuvants while not exhibiting the disadvantageous features of FCA.

EXAMPLE 4

Comparison Of A Novel Vaccine With Prior Art Glycopeptide Adjuvanted Vaccine

Three vaccines, each containing as antigen an oestradiol-3-0-carboxymethyl ether:human serum albumin conjugate were prepared with the following compositions per 2 ml dose:

Vaccine 1 (Freund's complete adjuvant emulsion) was prepared by dissolving antigen (1 mg) in saline (1 ml) and subsequently adding this to the oily FCA suspension whilst vortexing.

Vaccine 2 (DEAE-dextran emulsion immunoadjuvant) was prepared by dissolving antigen (1 mg) in 15% DEAE-dextran, pH 7.5 (1 ml) and subsequently adding this to an oily solution of Arlacel 80 (0.30 ml) in mineral oil (0.7 ml) whilst vortexing the mixture to produce the desired emulsion.

Vaccine 3 (a muramyldipeptide immunoadjuvant emulsion) was prepared according a published recipe (A. C. Allison and N. E. Byars, J. Immunol. Methods 1986, 95, 157-168) and was comprised of antigen (1 mg) and of muramyldipeptide (2 mg) dissolved in 2 ml of an emulsion composed of squalene (5% w/v), Pluronic L121 (2.5%) and 0.2% Tween 80 in saline.

Vaccine 1 thus represents a reference FCA vaccine. Vaccine 3 represents a state-of-the-art composition. Vaccine 2 is representative of the new art of this invention.

Figure 4:
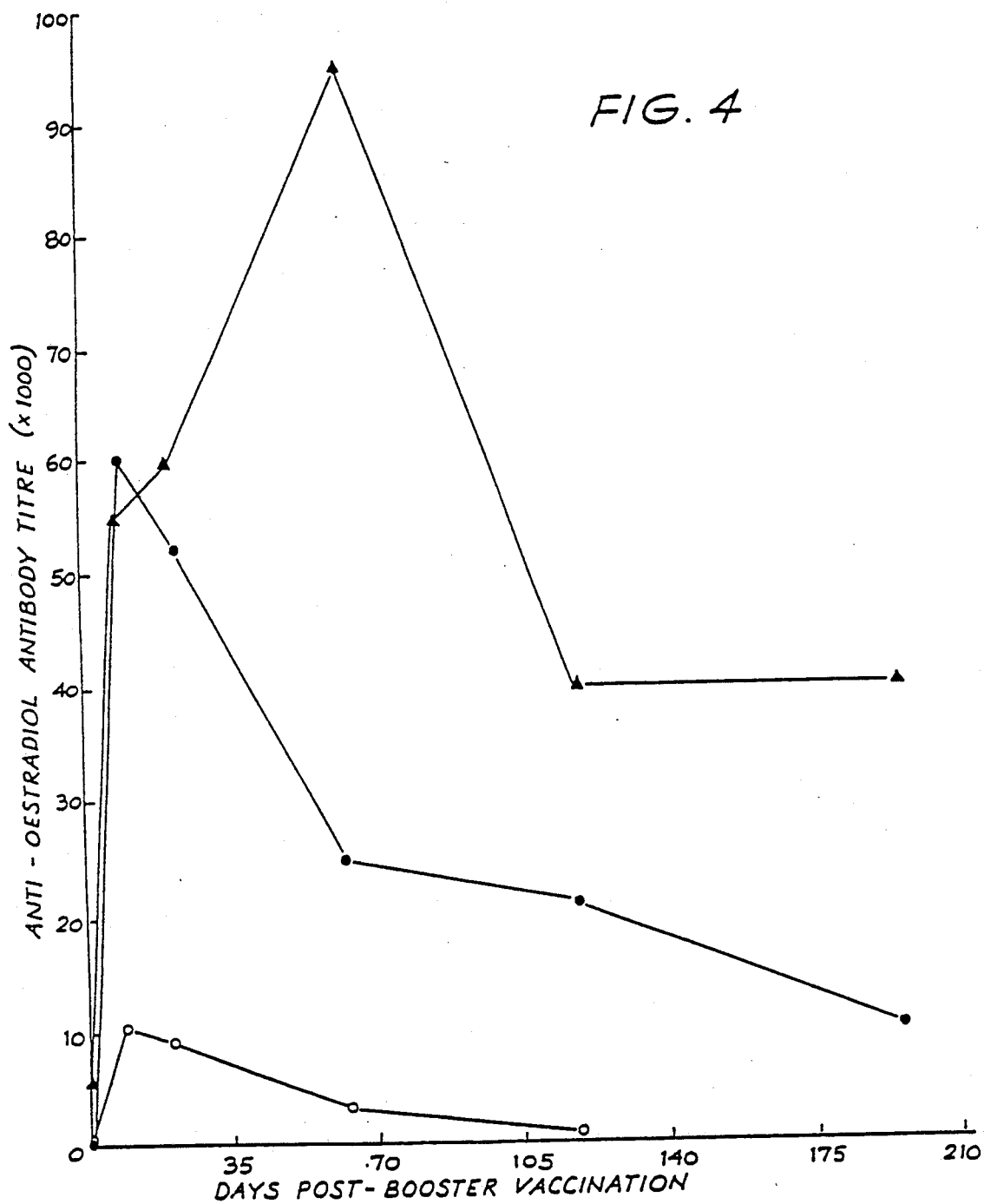
FIG. 4 shows the relationship between anti-oestradiol antibody titres and time following booster vaccination for three vaccines including one vaccine according to the present invention.

Three groups of sheep each comprising 12 Merino ewes, were vaccinated with Vaccines 1, 2 and 3 respectively. Each vaccination consisted of 2 ml vaccine given as 1 ml to each of two intramuscular hind leg sites. A primary vaccination was followed by a booster 6 weeks subsequently. Plasma samples were obtained from each ewe on the day of boost and 7, 21, 63, 119 and 196 days subsequently. The anti-oestradiol antibody titre was measured in each plasma sample and its mean for each vaccine shown on FIG. 4.

This example compares the new art of the invention with a glycopeptide adjuvant formulation, regarded by many as state-of-the-art vaccine technology for certain applications. It is clear that in relation to the peak antibody titre and the persistence of that titre the new art of the invention is superior to the glycopeptide adjuvant system.

EXAMPLE 5

Immunoadjuvant Activity Of Polyethyleneimine And Its Potentiation In Mineral Oil Emulsion Two vaccines, each containing as antigen an oestrone-3-0-carboxy-methylether:human serum albumin conjugate were prepared with the following compositions per 3 ml dose:

Vaccine 1 (Polyethyleneimine solution immunoadjuvant) was prepared by dissolving the antigen (1 mg) in pure water (2 ml) and then combining with 10% polyethyleneimine solution, pH 8, (1 ml).

Vaccine 2 (Polyethyleneimine emulsion immunoadjuvant) was prepared by dissolving antigen (1 mg) in 10% polyethyleneimine solution (pH 8, 1 ml) and subsequently adding this to mineral oil (0.75 ml) containing Arlacel 80 (0.25 ml) whilst vortexing in order to form the first emulsion. Subsequently 1% Tween 80 solution (1 ml) was added with continued vortexing to produce the desired emulsion.

Figure 5:
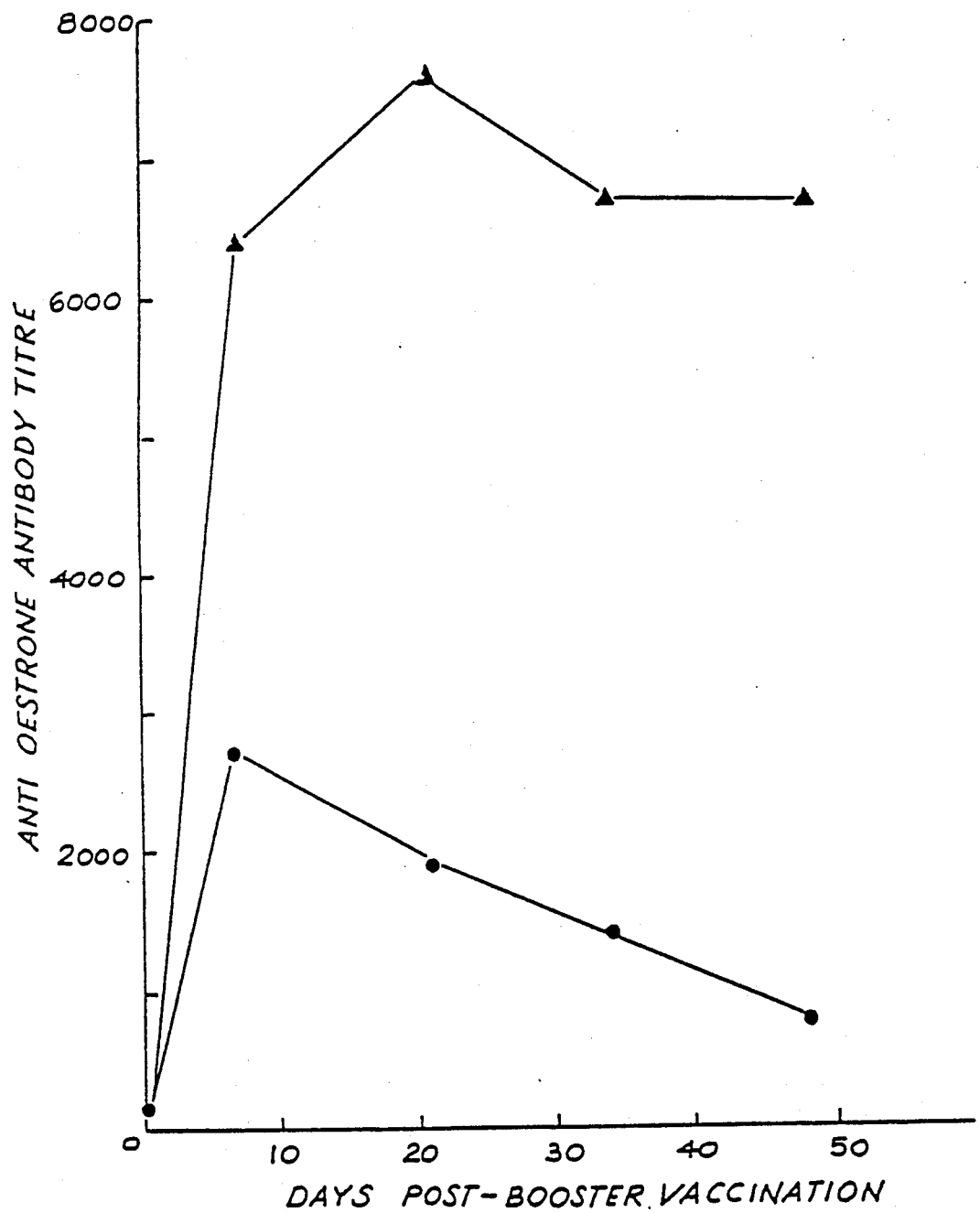
FIG. 5 shows the relationship between anti-oestrone antibody titres and time following a booster vaccination for two vaccines of which one is according to the present invention.

Two groups of sheep, each comprising 6 Merino ewes were vaccinated with Vaccines 1 and 2 respectively. Each vaccination consisted of 3 ml vaccine given as 1.5 ml to each of two subcutaneous sites located on either side of the neck. A primary vaccination was followed by a booster 5 weeks subsequently. Plasma samples were obtained from each ewe on the day of the boost and 7, 21, 34 and 48 days subsequently. The anti-oestrone antibody titre was measured in each plasma sample and mean values for each vaccine shown on FIG. 5.

This example demonstrates that polycationic polyelectrolytes other than DEAE-dextran, here polyethyleneimine, experience an augmentation of their immunostimulatory activity when formulated into emulsion vaccines according to this invention.

We claim:

1. An immunoadjuvant comprising:
   an oil phase, substantially free of mycobacteria; and
   an aqueous phase having a polycationic polyelectrolyte immunoadjuvant;
   wherein the oil phase and the aqueous phase are present in the ratio from 80:20 to 20:80 (v/v) and the polycationic polyelectrolyte immunoadjuvant is present in the aqueous phase in an amount from 5 to 25% weight to volume proportion.

2. An immunoadjuvant of claim 1, wherein the immunoadjuvant is in the form of an emulsion formed by the oil phase and the aqueous phase.

3. An immunoadjuvant as claimed in claim 2 in which the polycationic polyelectrolyte comprises a member of the group comprising diethylaminoethyl-dextran and polyethyleneimine.

4. An immunoadjuvant as claimed in claim 2 in which the oil is selected from the group comprising mineral oil, squalene and squalane.

5. An immunoadjuvant as claimed in claim 2 in which the emulsion is a water-in-oil emulsion.

* * * * *